(12) United States Patent
Miyamoto

(10) Patent No.: US 6,990,976 B2
(45) Date of Patent: Jan. 31, 2006

(54) ASTHMA DRUG INHALER WITH WHISTLE

(76) Inventor: Akihiko Miyamoto, 229-1, Furushiro, Makabemachi, Makabegun 300-4407, Ibaraki (JP)

( * ) Notice: Subject to any disclaimer, the term of this patent is extended or adjusted under 35 U.S.C. 154(b) by 0 days.

(21) Appl. No.: 10/658,744

(22) Filed: Sep. 10, 2003

(65) Prior Publication Data

US 2004/0089300 A1 May 13, 2004

(30) Foreign Application Priority Data

Oct. 22, 2002 (JP) ............................ 2002-306451
Apr. 25, 2003 (JP) ............................ 2003-121760

(51) Int. Cl.
 *A61M 11/00* (2006.01)
 *A61M 15/00* (2006.01)
 *A62B 9/00* (2006.01)

(52) U.S. Cl. .................... 128/200.23; 128/203.15; 128/205.23

(58) Field of Classification Search ............ 128/203.12, 128/203.15, 203.21, 203.22, 203.23, 205.23, 128/200.23, 200.24, 202.22; 604/58; 116/137 R
See application file for complete search history.

(56) References Cited

U.S. PATENT DOCUMENTS

| | | | | |
|---|---|---|---|---|
| 4,291,688 A | * | 9/1981 | Kistler .................... | 128/200.23 |
| 4,484,577 A | * | 11/1984 | Sackner et al. .......... | 128/203.28 |
| 5,522,380 A | * | 6/1996 | Dwork .................... | 128/200.23 |
| 5,758,638 A | * | 6/1998 | Kreamer ................. | 128/200.23 |
| 5,957,125 A | * | 9/1999 | Sagstetter et al. ...... | 128/200.23 |
| 6,039,042 A | * | 3/2000 | Sladek ................... | 128/200.23 |
| 6,427,688 B1 | * | 8/2002 | Ligotke et al. ......... | 128/203.15 |
| 6,523,536 B2 | * | 2/2003 | Fugelsang et al. ..... | 128/200.14 |
| 6,578,571 B1 | * | 6/2003 | Watt ....................... | 128/200.14 |
| 6,644,305 B2 | * | 11/2003 | MacRae et al. ......... | 128/200.21 |
| 6,698,422 B2 | * | 3/2004 | Fugelsang et al. ..... | 128/200.14 |
| 6,715,486 B2 | * | 4/2004 | Gieschen et al. ....... | 128/203.15 |
| 2005/0051161 A1 | * | 3/2005 | Anandampillai et al. ...................... | 128/200.23 |

OTHER PUBLICATIONS

McGavin, C.R. "A Modified Aerosol Inhaler for Teaching Technique." The Lancet, vol. 2, No. 7997, pp. 1227. Dec. 4, 1976.*

* cited by examiner

*Primary Examiner*—Teena Mitchell
(74) *Attorney, Agent, or Firm*—Westerman, Hattori, Daniels & Adrian, LLP

(57) ABSTRACT

An asthma drug inhaler is provided with a whistle. The whistle may be attached to a small opening for air intake. The air intake may be part of a mouthpiece located on an inhalation passage of finely powdered drug. The whistle makes a sound when the inhalation is properly done.

10 Claims, 16 Drawing Sheets

Fig.16
Prior Art
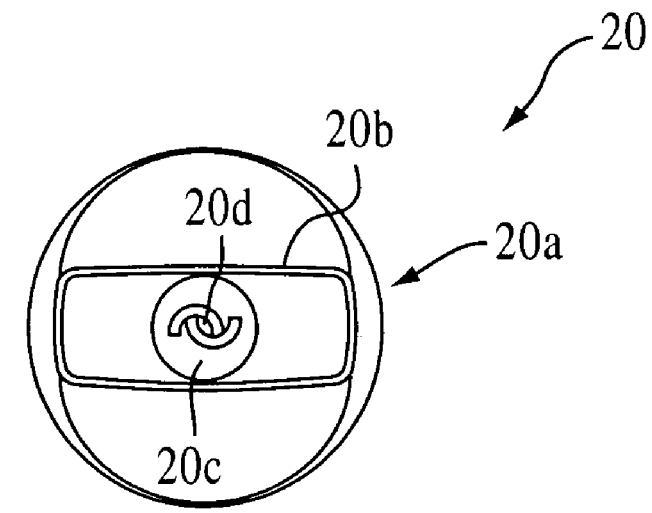
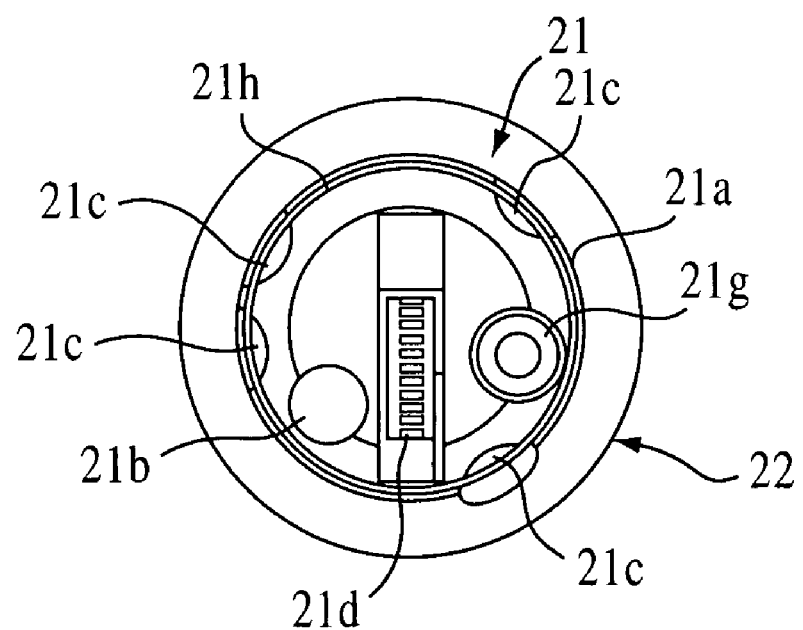

ASTHMA DRUG INHALER WITH WHISTLE

BACKGROUND OF THE INVENTION (i) Field of the Invention

The present invention is an asthma drug inhaler with a whistle, which makes a sound so as to allow a patient to check whether or not the drug inhalation can be appropriately accomplished without fault when the patient of the bronchial asthma inhales the finely powdered drug for asthma medication.

(ii) Description of the Related Art

Conventionally, as the antiasthmatic drug, the internal medicine had been mainly used. However, the asthma drug inhaler of the aerosol type was developed thereafter, with which the liquid medicine is misted by the use of a small tank charged with chlorofluorocarbon, and the patient inhales the misted medicine.

As is well known, the chlorofluorocarbon is the cause of the environmental destruction, and also, there is the concern over the effect on the human body. Therefore, the drug used in such a manner that the patient him/herself inhales the finely powdered drug has been increasingly brought into the mainstream. FIGS. 7 to 9 are the diagrams illustrating an example of the inhaler used in the manner that the drug is taken by the inhalation of the patient him/herself.

FIG. 7 is a front view of the conventional inhaler, FIG. 8 is a right side view of the conventional inhaler, and FIG. 9 is a plan view of the conventional inhaler. As shown in FIGS. 7 to 9, an asthma drug inhaler 9 is composed of a main body 9a, a disk cover 9b, a mouthpiece 10, a rotadisk 11 in which the finely powdered drug is individually packaged, and a small chamber 12.

As shown in FIGS. 7 to 9, small openings 10a and 10a are provided on both sides of the mouthpiece 10. The small openings 10a and 10a are used for taking air at the time of the inhalation.

More specifically, the small openings 10a are formed to correct the difference between the lung capacity in the inhalation and the air flow rate in the delivery passage of the finely powdered drug so as to prevent the breathing difficulty when taking air. If the small openings 10a are not provided, the patient will have the feeling of smothering when taking air.

The disk cover 9b is attached to the surface of the main body 9a, and a needle portion 9c is provided on the center of the upper part of the disk cover 9b. The needle portion 9c is used to open a hole 11a for the inhalation in the rotadisk 11 in which the drug is individually packaged. The reference numeral 9d denotes a semicircular protrusion.

When inhaling the drug with using the inhaler 9, by lifting the disk cover 9b immediately before its use, the needle portion 9c is stuck into a corresponding position of the rotadisk 11, in which the finely powdered drug is individually packaged. In this manner, the hole 11a is opened.

When the patient inhales the air through the mouthpiece 10 after opening the hole 11a, the drug flows into the small chamber 12 from the inside of the rotadisk 11 together with the air. The drug flown into the small chamber 12 and once dispersed therein is further dispersed after passing through a lattice 13 and delivered into the oral cavity through the mouthpiece 10.

In addition to the asthma drug inhaler 9 shown in FIGS. 7 to 9, there are several types of the inhaler having the structure that the finely powdered drug is inhaled by the patient him/herself. However, almost all of them have in common that the small openings for air intake are provided in the mouthpiece.

FIGS. 15 and 16 illustrate another conventionally used asthma drug inhaler 20, which is different from the asthma drug inhaler 9 shown in FIGS. 7 to 9. The asthma drug inhaler 20 of this example is formed of a cylindrical main body 21 and a mouthpiece 20a attached thereto.

In the asthma drug inhaler 20, four air-intake apertures 21c are provided in the upper part of the outer peripheral surface of a tube body 21a of the cylindrical main body 21, and an air hole 21e is provided in an engaging portion 21f attached to the lower part of the tube body 21a. An inhaled drug tube 21b, a scale 21d, and a drug reservoir tube 21g are provided inside the tube body 21a, and a partition lid 21h is attached to the upper part of the tube body 21a. The mouthpiece 20a is attached to the partition lid 21h.

In the case where the patient inhales the asthma drug by the use of the asthma drug inhaler 20 by him/herself, when the patient inhales the air after holding an upper part 20b of the mouthpiece 20a in the mouth, the air flown in through the air hole 21e winds up the drug in the inhaled drug tube 21b and flows into the mouthpiece 20a through a drug inlet 20d of the mouthpiece 20a to generate the spiral flow in a spiral-shaped groove 20c, by which the finely powdered drug is dispersed and delivered into the oral cavity.

At this time, air is taken through the air-intake apertures 21c to correct the difference between the lung capacity in the inhalation and the air flow rate in the delivery passage of the finely powdered drug so as to prevent the breathing difficulty when taking air.

As described above, the conventionally used asthma drug inhalers can be largely classified into the two types as follows, that is, the type as shown in FIGS. 7 and 9, in which air is taken through the small openings provided in the mouthpiece, more specifically, air is taken from the lower stream of the air passage, and the type as shown in FIGS. 15 and 16, in which air is taken from the lower part and the upper part of the main body located below the mouthpiece, more specifically, air is taken from the upper stream of the air passage.

SUMMARY OF THE INVENTION

However, not only in the inhaler 9 shown in FIGS. 7 to 9 and the inhaler 20 shown in FIGS. 15 and 16 but also in the inhaler with a structure that the finely powdered drug is inhaled by the patient him/herself, the amount of the finely powdered drug is extremely small. Therefore, such inhalers have the disadvantages that the patient cannot check whether or not the drug inhalation can be appropriately accomplished.

In addition, the actual situation is that the patients are in many cases the children and the elderly who cannot handle the inhaler and blow the mouthpiece by mistake and thus the drug does not effect properly on the patients.

In such a circumstance, an object of the present invention is to provide an asthma drug inhaler capable of checking whether or not the inhalation is properly done in each use both objectively and by the user him/herself, while making the best use of the advantages of the above-mentioned medical device.

For the solution of the problem mentioned above, the asthma drug inhaler with a whistle according to the present invention comprises a whistle attached to the small opening for air intake provided at a part of a mouthpiece located on the inhalation passage of the finely powdered drug, wherein the whistle makes a sound when the inhalation is properly done, and also, the asthma drug inhaler with a whistle according to the present invention comprises a whistle attached to an air intake provided on the upper stream of the passage of the air for winding up the finely powdered drug, wherein the whistle makes a sound when the inhalation is properly done.

BRIEF DESCRIPTION OF THE DRAWINGS

FIG. 16 is an exploded plan view of the conventional inhaler of FIG. 15.

DESCRIPTION OF THE PREFERRED EMBODIMENTS

Hereinafter, the asthma drug inhaler with a whistle according to the present invention will be described in detail based on the accompanying drawings.

Figure 1:
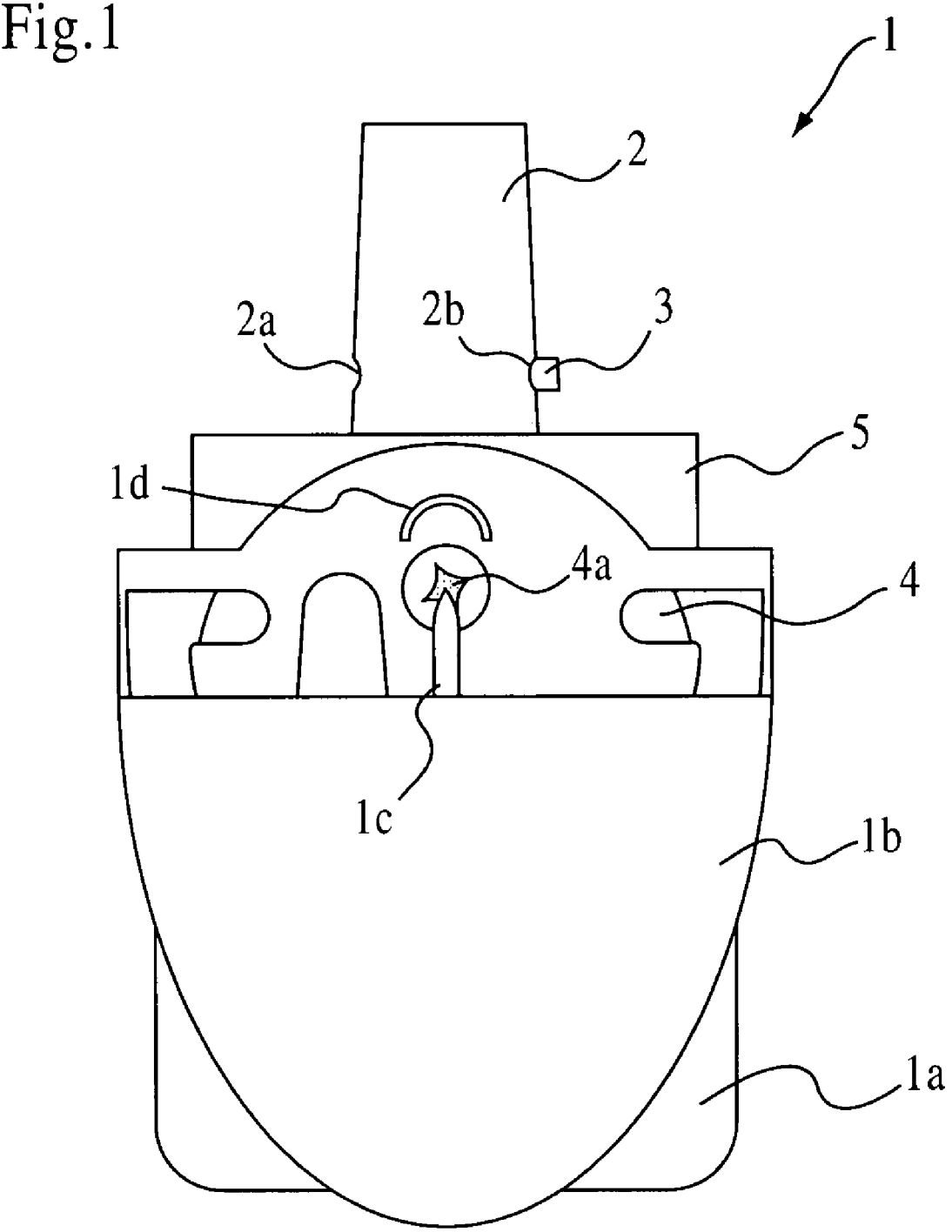
FIG. 1 is a front view of an asthma drug inhaler with a whistle according to the present invention.
Figure 2:
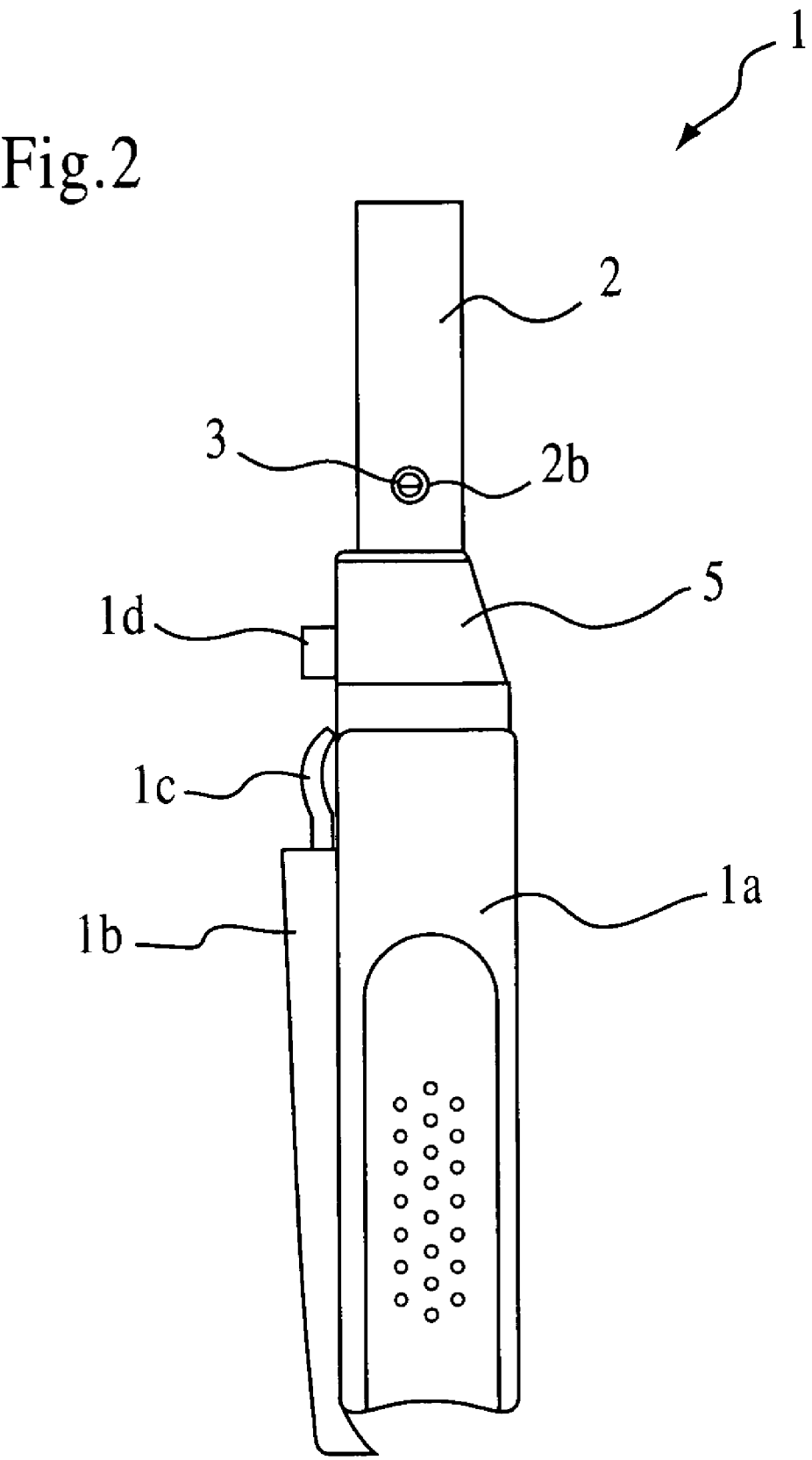
FIG. 2 is a right side view of the asthma drug inhaler of FIG. 1 with a whistle according to the present invention.
Figure 3:
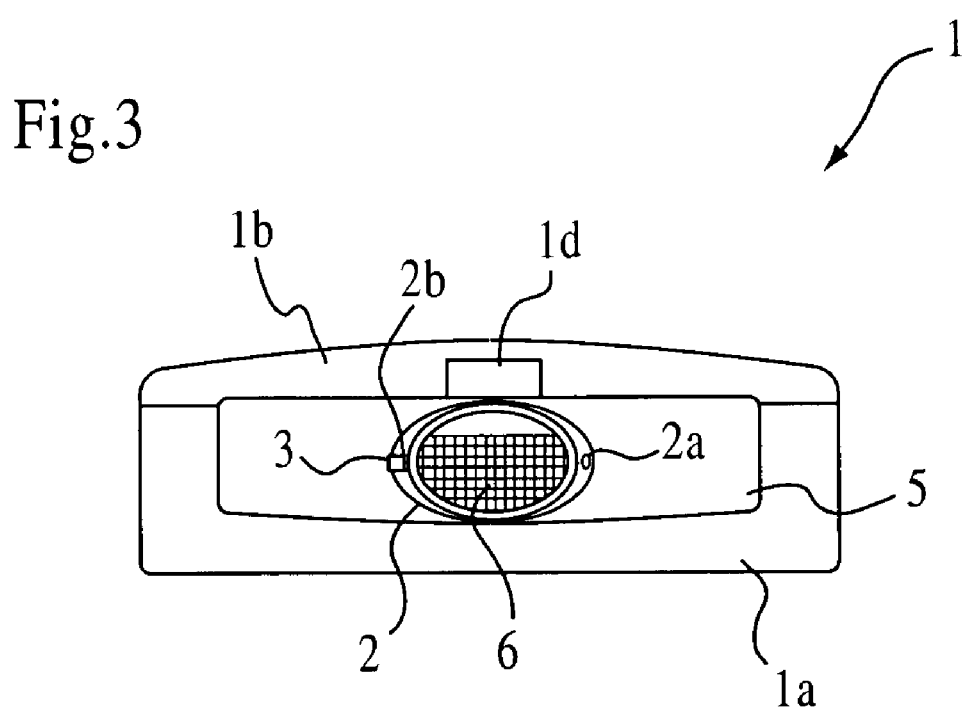
FIG. 3 is a plan view of the asthma drug inhaler of FIG. 1 with a whistle according to the present invention.

FIG. 1 is a front view of the asthma drug inhaler with a whistle according to the present invention, FIG. 2 is a right side view of the asthma drug inhaler with a whistle according to the present invention, and FIG. 3 is a plan view of the asthma drug inhaler with a whistle according to the present invention.

As shown in FIGS. 1 to 3, the asthma drug inhaler with a whistle 1 according to the present invention is composed of a main body 1a, a disk cover 1b, a rotadisk 4 in which the finely powdered drug is individually packaged, a small chamber 5, a mouthpiece 2 and a whistle 3 attached to the mouthpiece.

The rotadisk 4 in which the finely powdered drug is individually packaged is set in the main body 1a of the asthma drug inhaler with a whistle 1, the disk cover 1b is provided to the surface of the main body 1a so as to cover the rotadisk 4, and a needle portion 1c is provided at the center of the upper part of the disk cover 1b.

The needle portion 1c is used to open a hole 4a for the inhalation of the drug in the rotadisk 4 in which the drug is individually packaged. The needle portion 1c is stuck into a corresponding position of the rotadisk 4 by lifting the disk cover 1b, thereby opening the hole 4a.

As shown in FIG. 1, a left small opening 2a and a right small opening 2b are provided on both sides of the mouthpiece 2. The left and right small openings 2a and 2b are used for taking air at the time of the inhalation. More specifically, the left and right small openings 2a and 2b are formed to correct the difference between the lung capacity in the inhalation and the air flow rate in the delivery passage of the finely powdered drug so as to prevent the breathing difficulty when taking air.

If the left and right small openings 2a and 2b are not provided or the left and right small openings are blocked, since the patient will have the feeling of smothering when taking air, such an inhaler is inappropriate.

In the asthma drug inhaler with a whistle 1 according to the present invention, of the left and right small openings 2a and 2b provided in the mouthpiece, the whistle 3 is attached to the small opening 2b on the right side.

The whistle 3 is designed to make a sound when air flows through the whistle 3 at the time of inhalation. More specifically, the whistle 3 makes a sound when the inhalation can be done appropriately without blowing the mouthpiece by mistake. Note that the whistle 3 can be attached to either of the left small opening 2a or the right small opening 2b provided in the mouthpiece.

As shown in FIG. 3, a lattice 6 is provided on the border between the mouthpiece 2a and the small chamber 5. The finely powdered drug from the rotadisk 4 flown into the small chamber 5 together with the air and dispersed therein at the time of inhalation is further dispersed after passing through the lattice 6 and delivered into the oral cavity.

Figure 4:
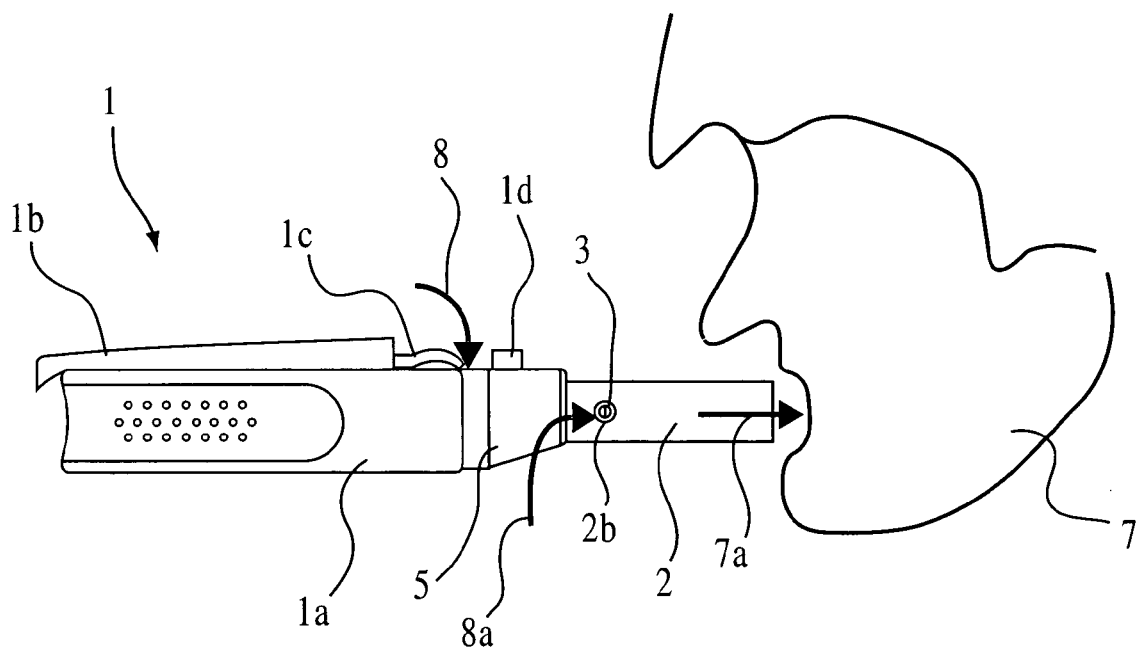
FIG. 4 is a diagram showing the state where the drug is inhaled by the use of the asthma drug inhaler of FIG. 1 with a whistle according to the present invention.
Figure 5:
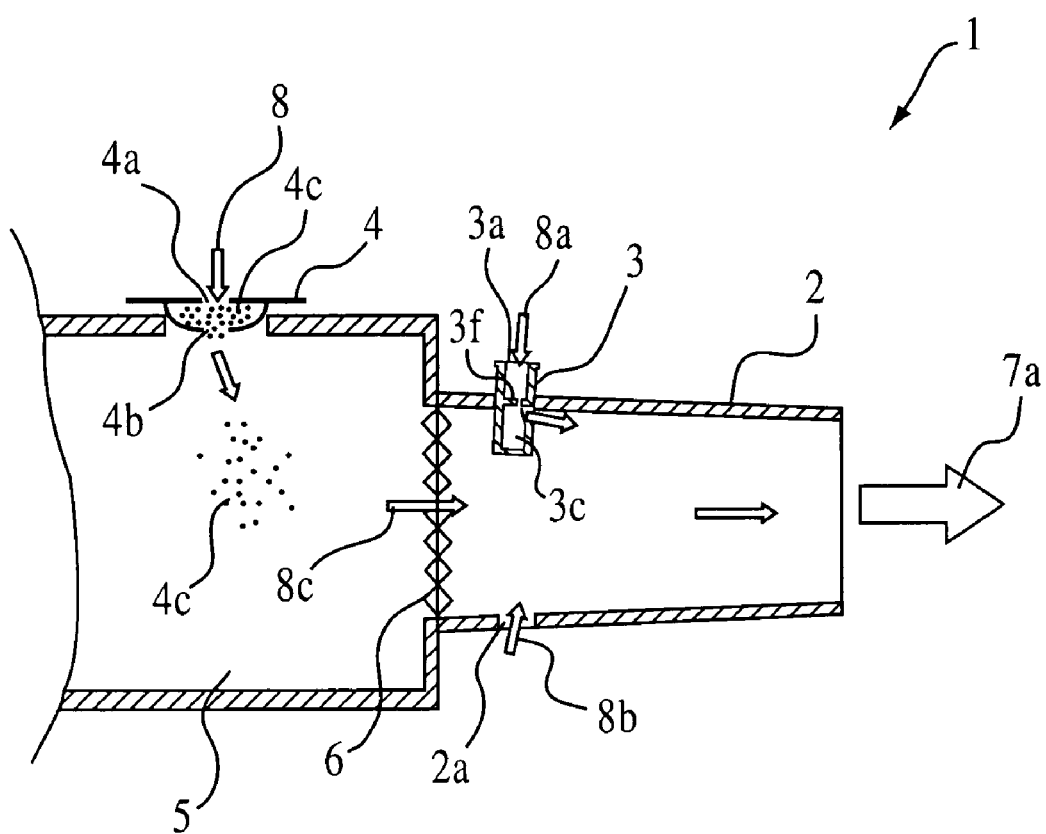
FIG. 5 is a partially enlarged sectional view showing the state where the drug is inhaled by the use of the asthma drug inhaler of FIG. 1 with a whistle according to the present invention.
Figure 6:
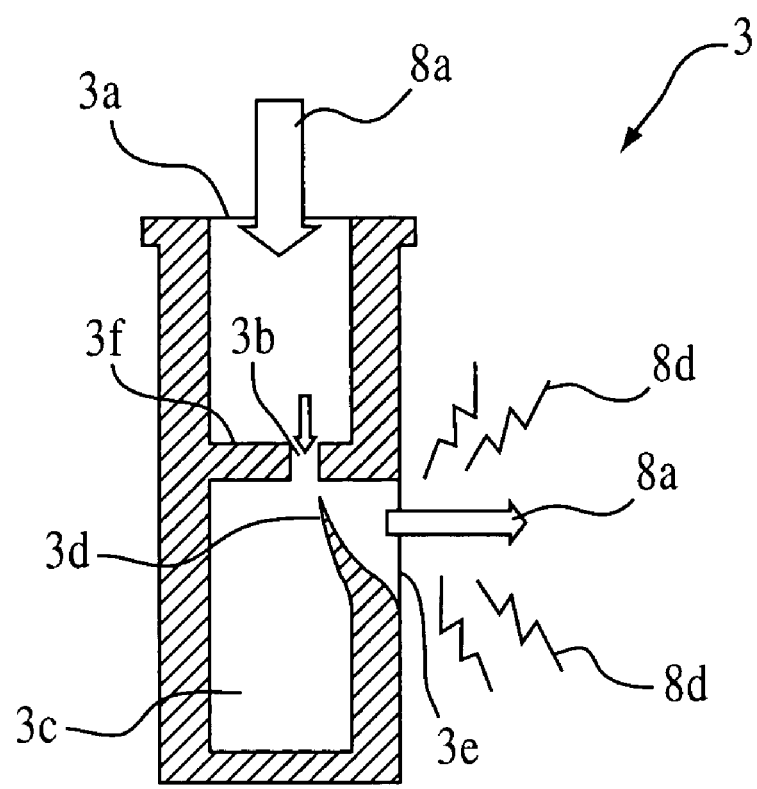
FIG. 6 is an enlarged sectional view of the whistle portion of FIG. 1.

FIG. 4 is a diagram showing the state where the drug is inhaled by the use of the asthma drug inhaler with a whistle according to the present invention, FIG. 5 is a partially enlarged sectional view showing the state where the drug is inhaled by the use of the asthma drug inhaler with a whistle according to the present invention, and FIG. 6 is an enlarged sectional view of the whistle portion.

As shown in FIGS. 4 and 5, when a patient 7 inhales the drug with using the asthma drug inhaler with a whistle 1, it is necessary to open a front surface hole 4a and a bottom surface hole 4b by lifting the disk cover 1b to strike the tip of the needle portion 1c into a corresponding position of the rotadisk 4 immediately before its use.

After opening the hole 4a, the patient 7 holds the mouthpiece 2 of the asthma drug inhaler with a whistle 1 in his/her mouth and inhales the air 7a. Then, the air 8 flows in through the front surface hole 4a provided in the rotadisk 4, and the finely powdered drug 4c together with the air 8 flows into the small chamber 5 of the asthma drug inhaler with a whistle 1 through the bottom surface hole 4b provided at the bottom of the rotadisk 4.

When the patient 7 inhales the air 7a, at the same time with the inflow of the air 8 through the hole 4a, the air 8a and 8*b* are also taken through the left small opening 2*a* and the right small opening 2*b* provided in the mouthpiece 2 to correct the difference between the lung capacity in the inhalation and the air flow rate in the delivery passage or the air.

At this time, since the whistle 3 is attached to the right small opening 2*b*, the air 8*a* passes through the whistle 3 when the air 8*a* is taken in the mouthpiece 2, and the whistle 3 makes a sound.

As shown in FIGS. 5 and 6, an air inlet 3*a* is formed in the upper portion of the bottomed whistle 3 with a cylindrical shape, a partition wall 3*f* is formed inside it, and an air vent 3*b* is provided in the partition wall 3*f*. A hollow resonant chamber 3*c* is formed below the partition wall 3*f*. In addition, a protrusion 3*d* having a sharp, tapered top and slightly bent toward the resonant chamber 3*c* is formed below the air vent 3*b*. It is also possible to form the whistle 3 by a bottomed square tube or a bottomed polygonal tube.

The air 8*a* flown in the whistle 3 through the air inlet 3*a* swiftly passes through the narrow air vent 3*b* and hits the protrusion 3*d* provided in the air outlet 3*e*, and the vibration of the air generated at this moment is resonated in the resonant chamber 3*c*. In this manner, a sound 8*d* like "beep" is emitted from the air outlet 3*e* together with the air 8*a*.

As described above, the air 8*a* flows in the whistle 3 through the air inlet 3*a* and flows out from the whistle 3 through the air outlet 3*e*. Therefore, the air 8*a* is taken in without interfering the function of the small opening 2*b* for air intake provided in the mouthpiece 2.

At this time, if the patient blows the mouthpiece by mistake or the inhalation of the air is insufficient, the sufficient amount of air is not taken in the whistle 3. Therefore, the sound 8*d* is not emitted from the whistle 3. The sound 8*d* is emitted from the whistle 3 only when the sufficient amount of air can be taken. In this manner, the patient 7 him/herself who has inhaled the drug and the persons close to the patient can check whether or not the drug is appropriately inhaled.

The whistle 3 is designed to be detachable. Therefore, when the patient 7 begins the medication by the use of the inhaler, the patient 7 can use the asthma drug inhaler with a whistle 1 with the whistle 3 being attached, and the patient 7 can use the inhaler without attaching the whistle 3 after the patient 7 gets accustomed to handling the inhaler.

Figure 7:
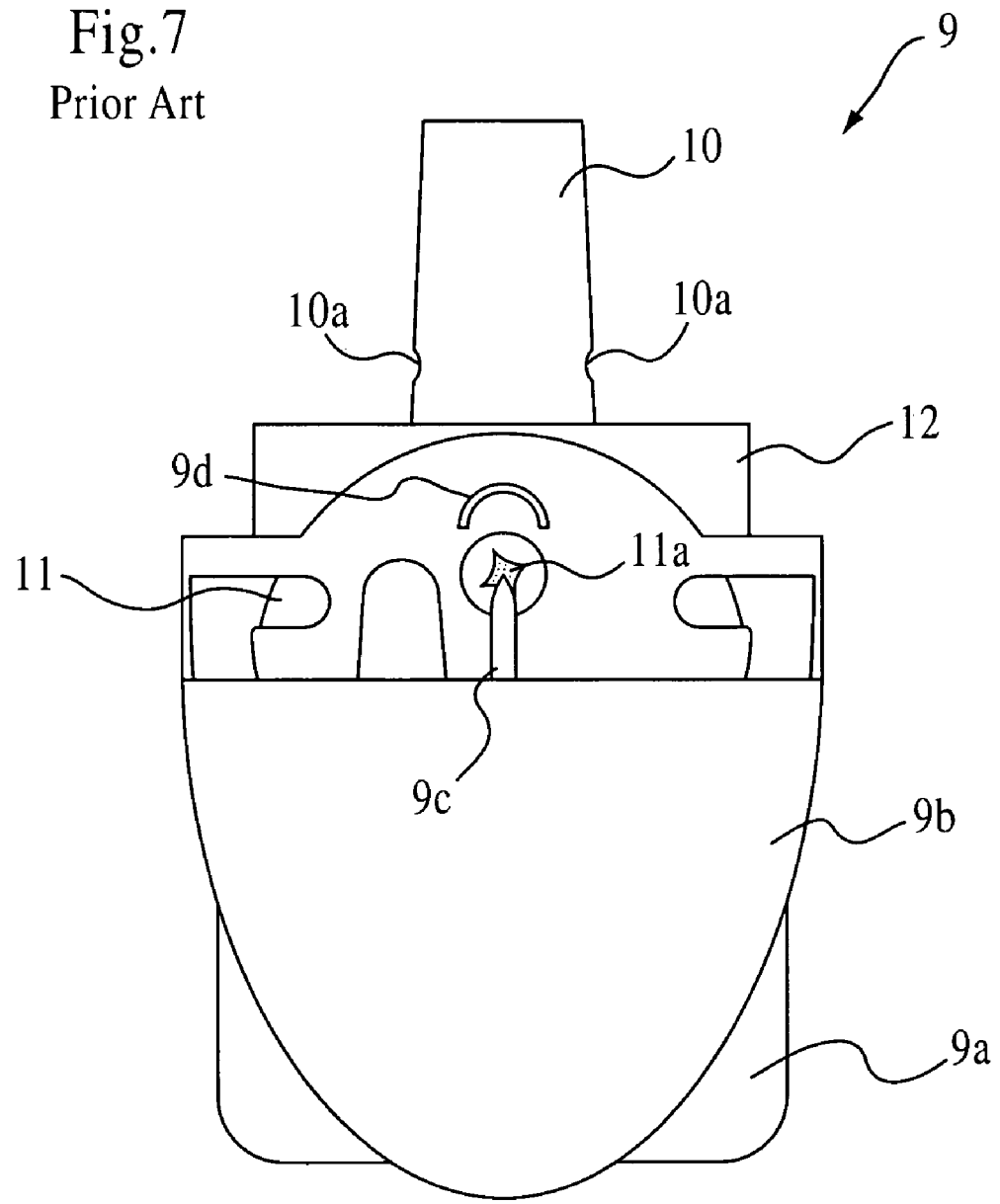
FIG. 7 is a front view of a conventional inhaler.
Figure 8:
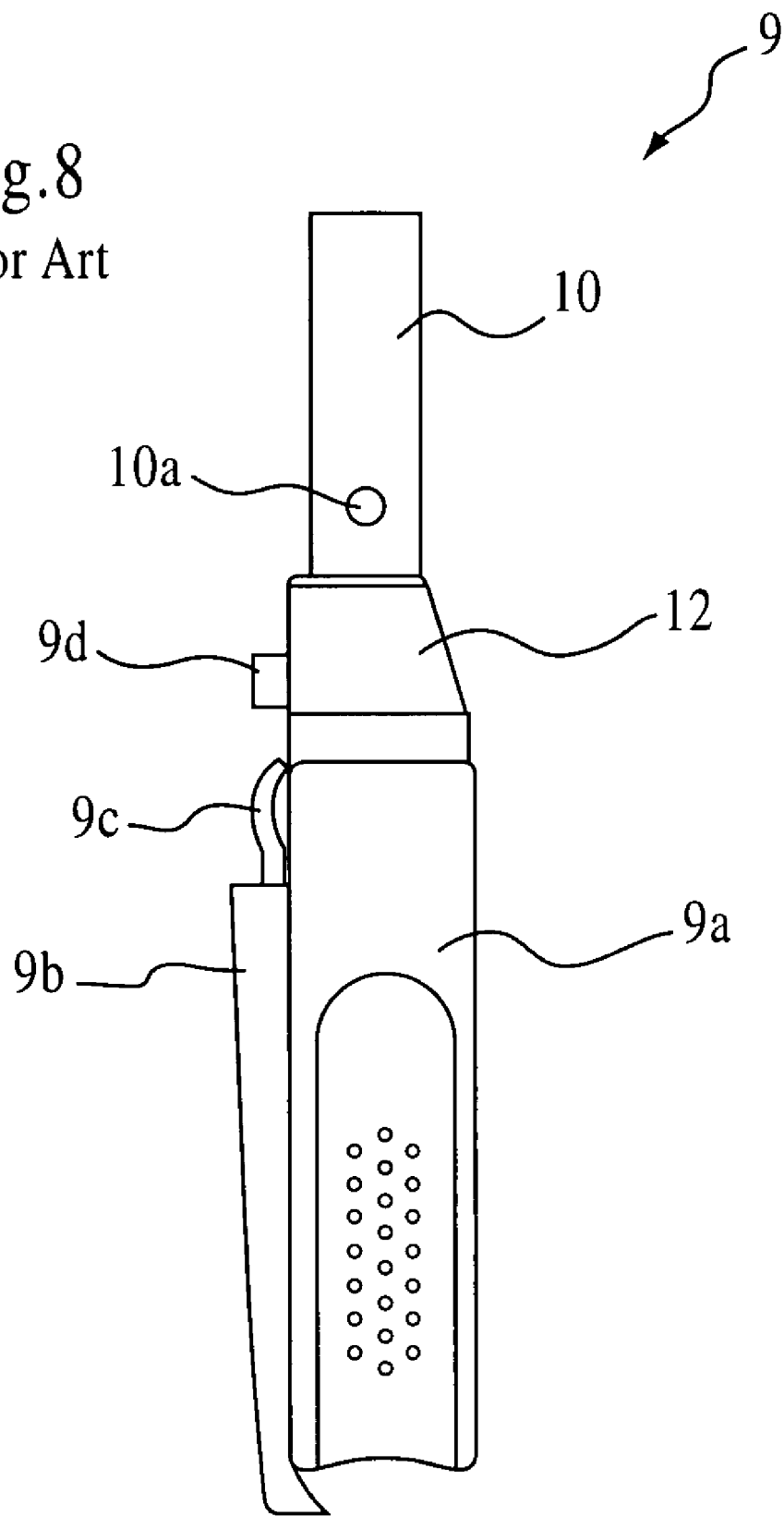
FIG. 8 is a right side view of the conventional inhaler of FIG. 7.
Figure 9:
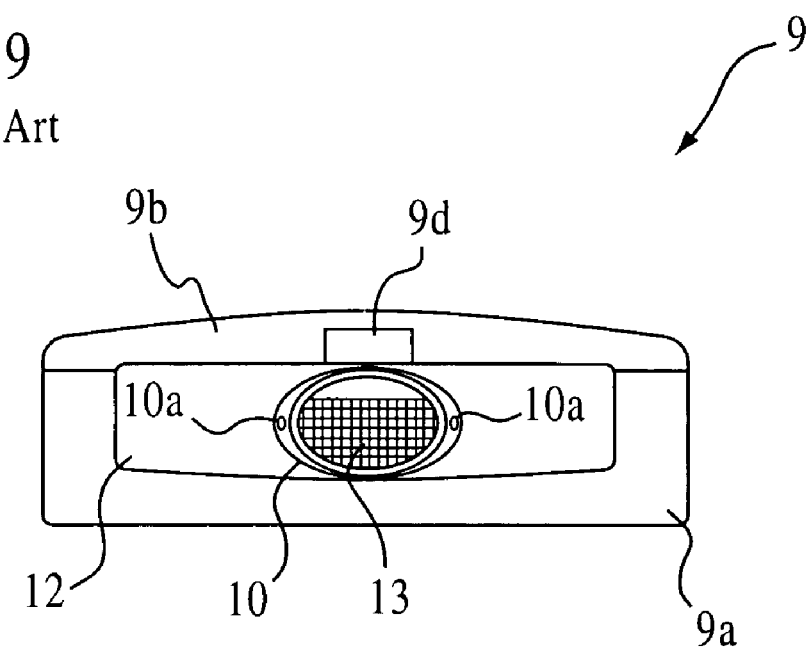
FIG. 9 is a plan view of the conventional inhaler of FIG. 7.

Furthermore, since the whistle 3 is designed to be detachable as described above, the asthma drug inhaler with a whistle 1 shown in FIGS. 1 to 6 is realized by attaching the whistle 3 to the conventional asthma drug inhaler 9 shown in FIGS. 7 to 9.

However, not only the asthma drug inhaler 9 but also the other inhalers can be used to provide the asthma drug inhaler with a whistle by attaching a whistle to a small opening for air intake if the inhalers have a structure in which a small opening for air intake is provided on a delivery passage of the drug such as a mouthpiece and the finely powdered drug is inhaled by the patient him/herself, more specifically, if the inhaler has a structure in which the air is taken in from the spiral flow portion of the air passage.

FIGS. 10 to 14 are diagrams showing an asthma drug inhaler with a whistle according to another embodiment of the present invention. As shown in FIGS. 10 to 14, the asthma drug inhaler with a whistle according to this embodiment is realized by attaching a whistle to the conventional asthma drug inhaler shown in FIGS. 15 and 16.

Figure 10:
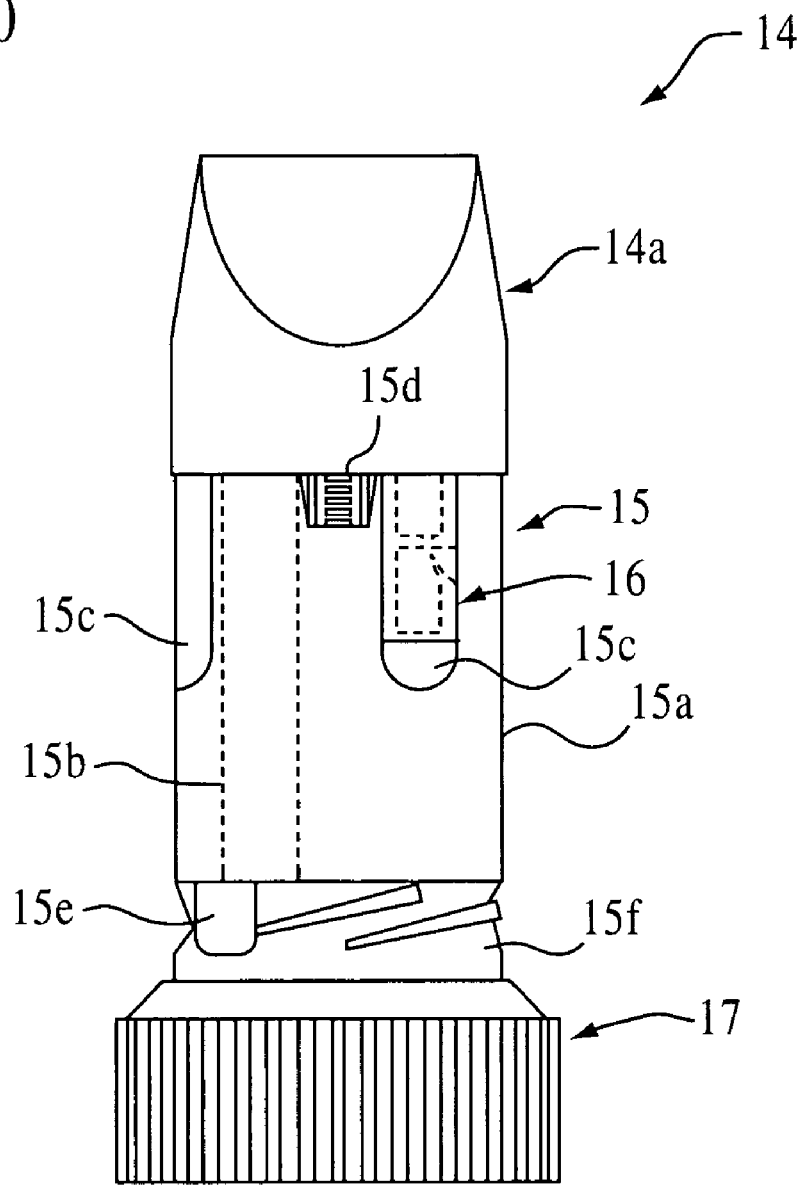
FIG. 10 is a front view of an asthma drug inhaler with a whistle according to another embodiment of the present invention.
Figure 11:
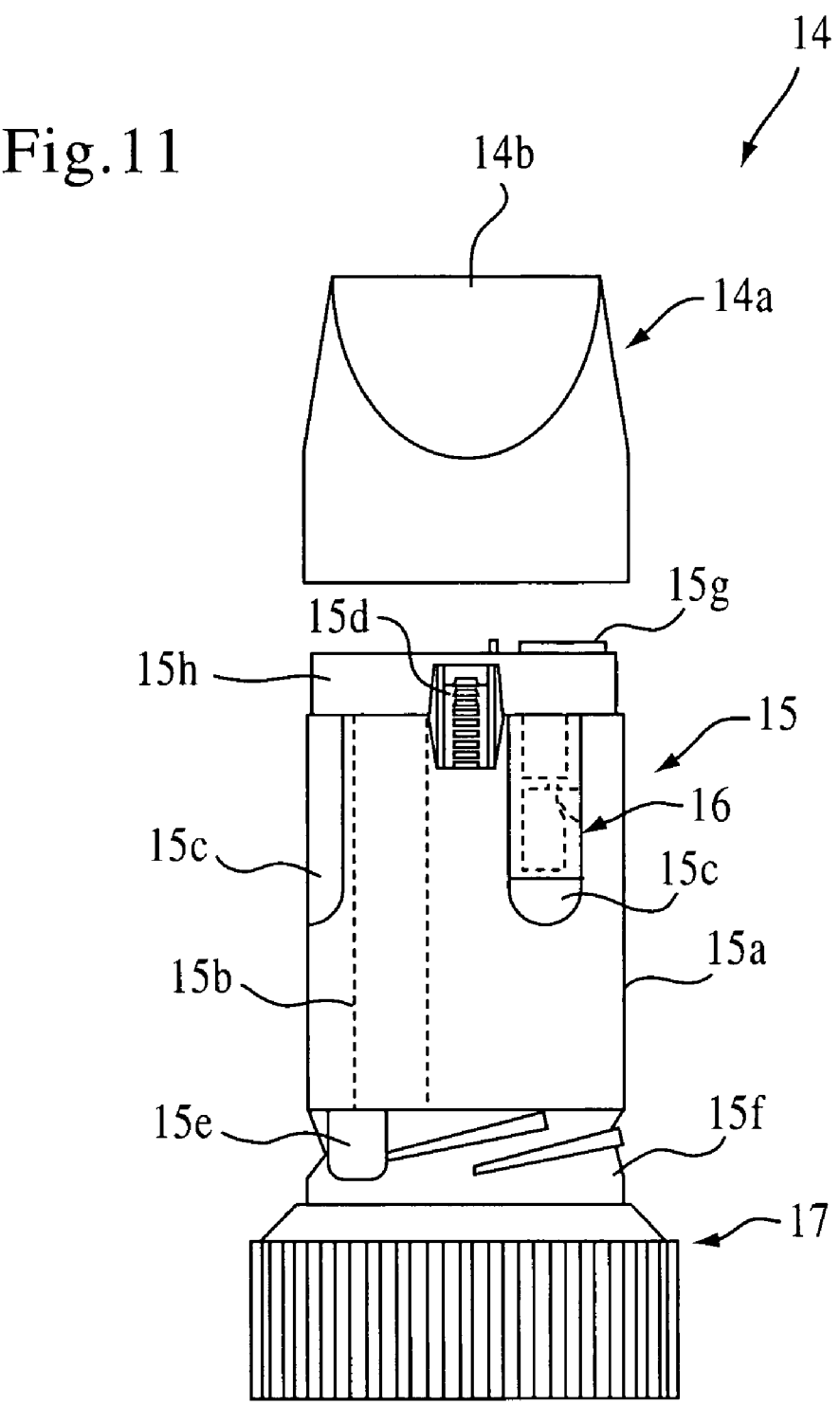
FIG. 11 is an exploded front view of the asthma drug inhaler of FIG. 10 with a whistle according to another embodiment of the present invention.
Figure 12:
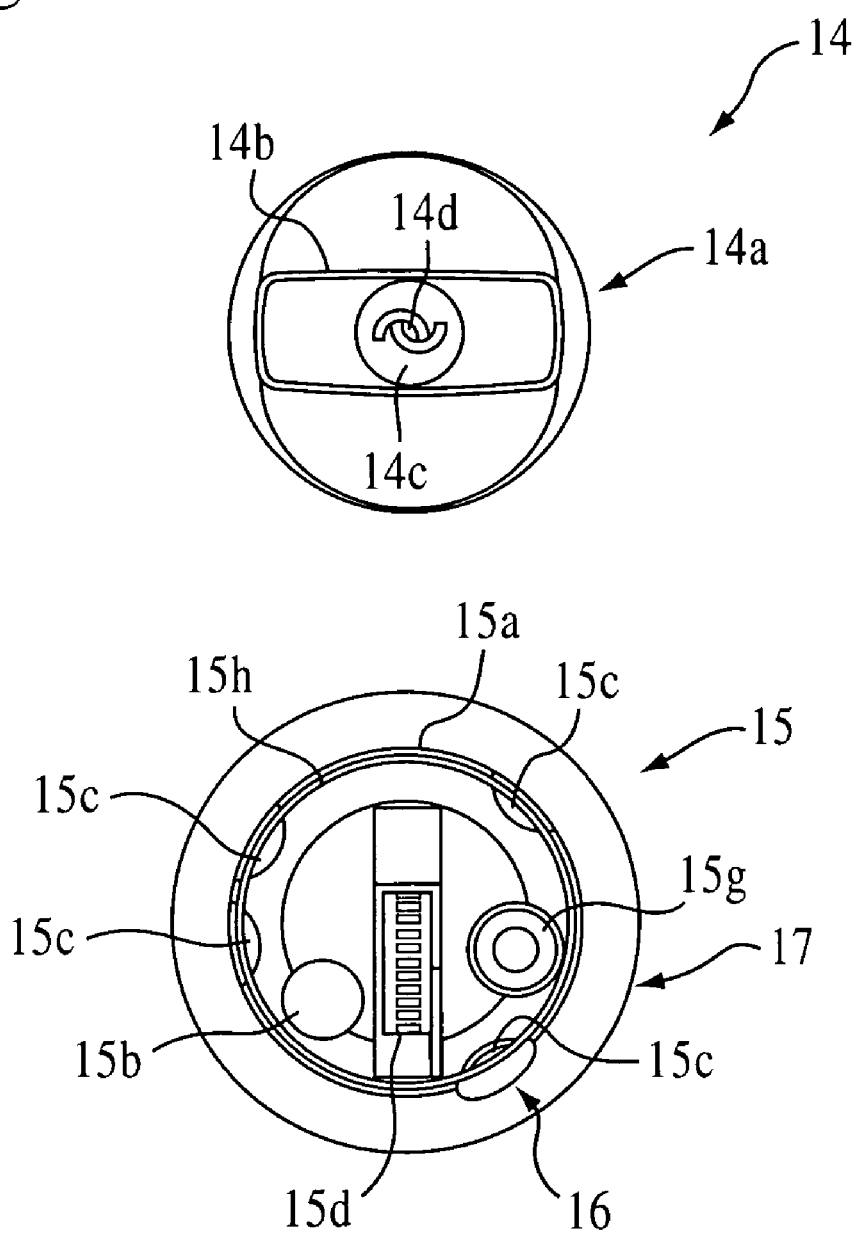
FIG. 12 is an exploded plan view of the asthma drug inhaler of FIG. 10 with a whistle according to another embodiment of the present invention.

FIG. 10 is a front view of the asthma drug inhaler with a whistle according to another embodiment of the present invention, FIG. 11 is an exploded front view of the asthma drug inhaler with a whistle according to another embodiment of the present invention, and FIG. 12 is an exploded plan view of the asthma drug inhaler with a whistle according to another embodiment of the present invention.

As shown in FIG. 10, the asthma drug inhaler with a whistle 14 according to this embodiment of the present invention is composed of a mouthpiece 14*a*, a main body 15, a whistle 16, and a support 17. Also, as shown in FIG. 11, the mouthpiece 14*a* is designed to be detachable from the main body 15 of the asthma drug inhaler with a whistle 14.

Hereinafter, the structure of the asthma drug inhaler with a whistle 14 will be described based on FIGS. 11 and 12 each showing the front view and the plan view of the asthma drug inhaler with a whistle 14 in a state where the mouthpiece 14*a* is detached from the main body 15.

As shown in FIGS. 11 and 12, the mouthpiece 14*a* of the asthma drug inhaler with a whistle 14 according to this embodiment has a front surface and a rear surface tapered toward an upper portion 14*b* to be held in the mouth.

As shown in the plan view, the upper portion 14*b* has an approximately rectangular shape. In the upper portion 14*b* with an approximately rectangular shape, a spiral-shaped groove 14*c* for generating a spiral flow is formed and a drug inlet 14 penetrating through it is formed at the center of the groove 14*c*. In the asthma drug inhaler with a whistle 14 according to this embodiment, the cylindrical main body 15 is supported by the support 17.

In the cylindrical main body 15, four air-intake apertures 15*c* for taking air with an oblong shape are provided in the upper part of the outer peripheral surface of a tube body 15*a*, and an air hole 15*e* is provided in an engaging portion 15*f* attached to the lower part of the tube body 15*a*. Although not shown, the engaging portion 15*f* is a part with which a cover is engaged when setting a cover for covering the main body 15.

A partition lid 15*h* is attached to the upper part of the tube body 15*a*, and the upper end of the cylindrical inhaled drug tube 15*b* provided inside the tube body 15*a* is protruded from the top of the partition lid 15*h*. In addition, the upper end of a drug reservoir tube 15*g* similarly provided inside the tube body 15*a* is protruded from the top of the partition lid 15*h*, and a cap is fitted to the upper end of the drug reservoir tube 15*g* so as to prevent the leakage of the drug.

The whistle 16 is attached to one of the four air-intake apertures 15*c* provided in the upper part of the outer peripheral surface of the main body 15. The whistle 16 is designed to be detachable, and it is possible to attach the whistle 16 to any one of the four air-intake apertures 15*c*. The structure of the whistle 16 is identical to that of the whistle 3 shown in FIG. 6. Note that the reference numeral 15*d* denotes a scale.

Figure 13:
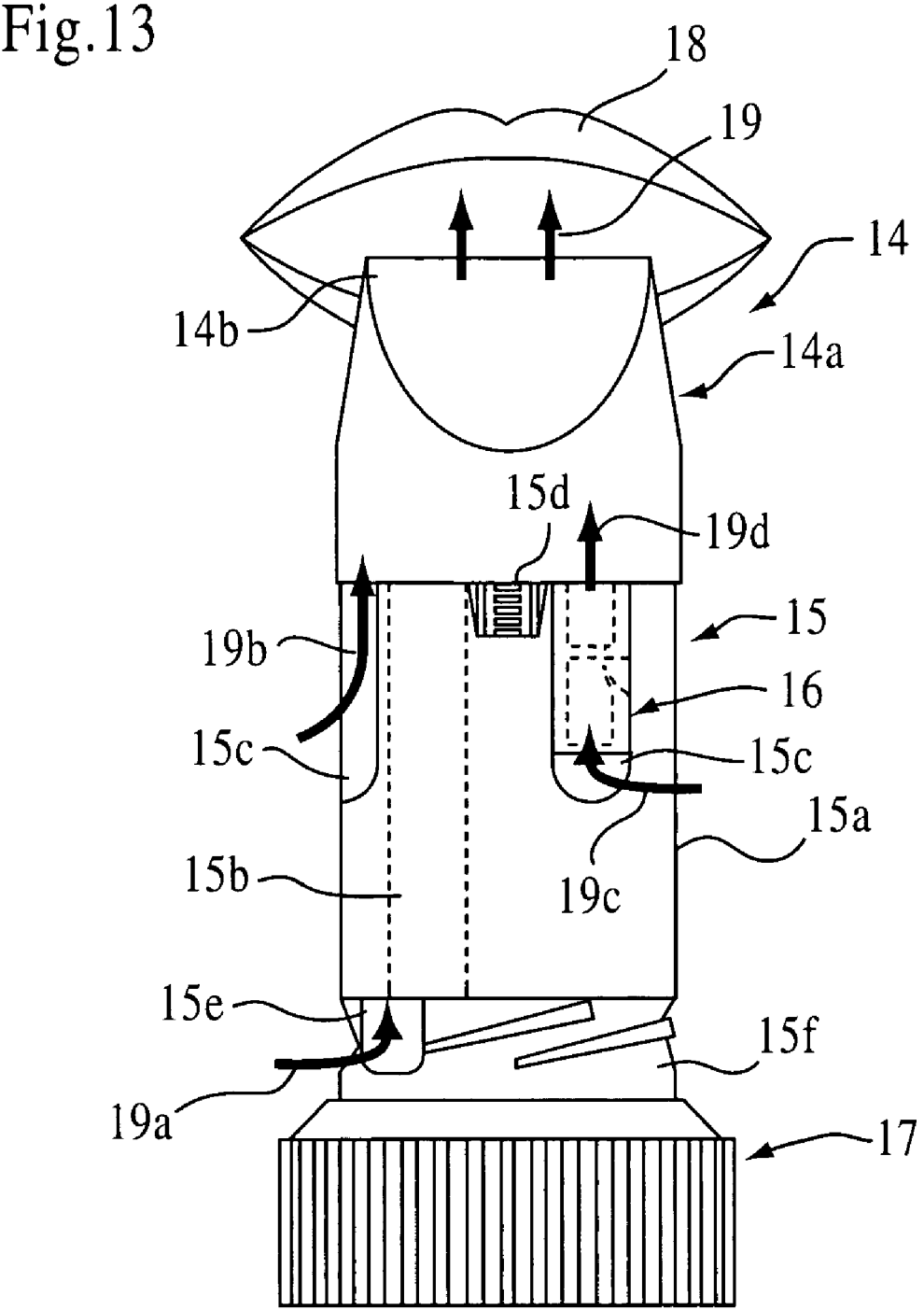
FIG. 13 is a diagram showing the state where the drug is inhaled by the use of the asthma drug inhaler of FIG. 10 with a whistle according to another embodiment of the present invention.
Figure 14:
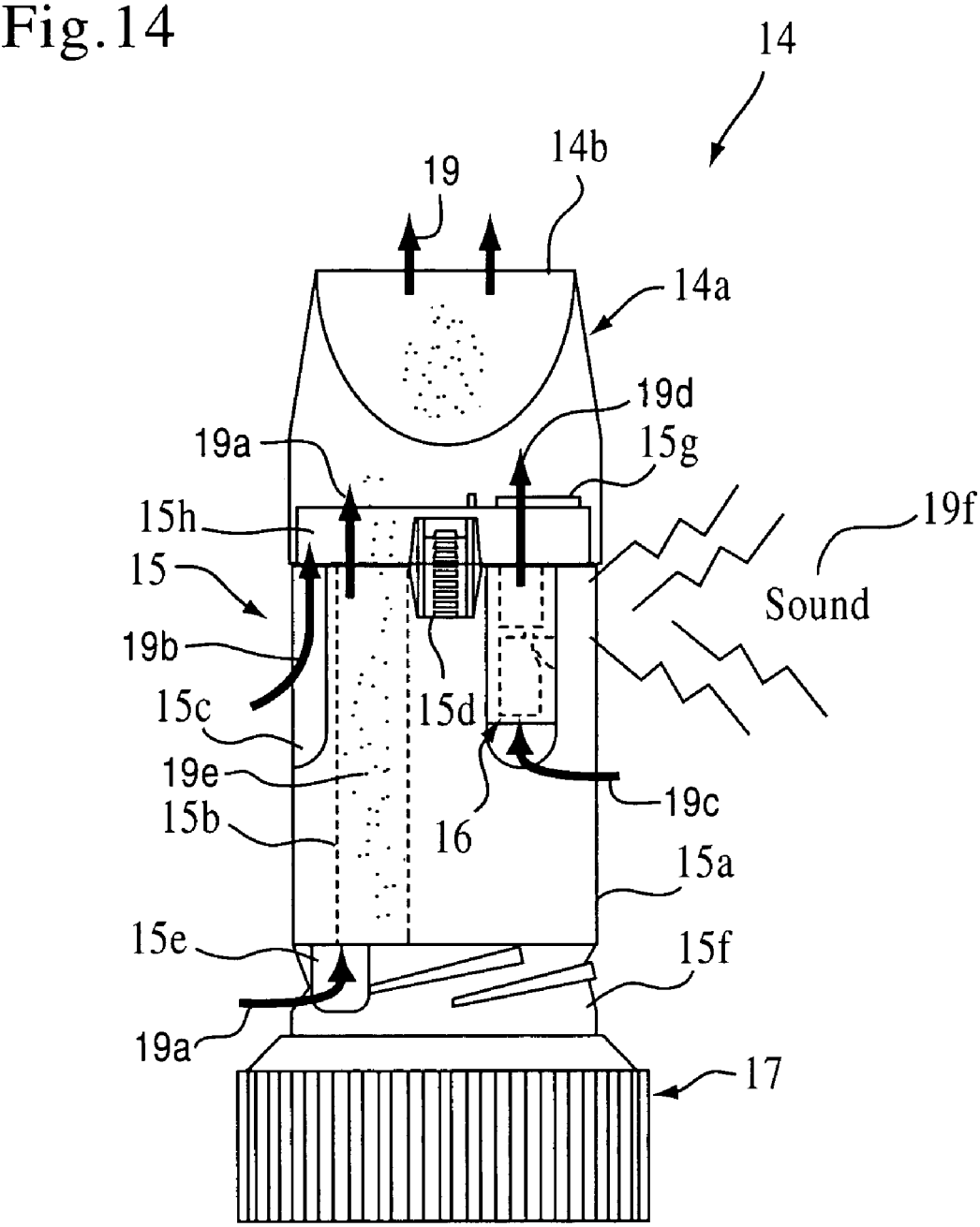
FIG. 14 is a diagram showing the flow inside the inhaler of FIG. 13.

FIG. 13 is a diagram showing the state where the drug is inhaled by the use of the asthma drug inhaler with a whistle according to another embodiment of the present invention, and FIG. 14 is a diagram showing the flow inside the inhaler. As shown in FIG. 13, when the patient him/herself inhales the asthma drug by the use of the asthma drug inhaler with a whistle 14, first, the patient holds the mouthpiece 14*a* in his/her mouth 18 and inhales air. The reference numeral 19 denotes the air inhaled in the mouth.

When the patient takes the air with holding the mouthpiece 14*a* in the mouth 18, the air 19*a* flows in through the air hole 15*e* provided at the lower part of the main body 15, and further, the air 19*b* and 19*c* also flow in through the four air-intake apertures 15*c* provided in the upper part of the tube body 15*a* to correct the difference between the lung capacity in the inhalation and the air flow rate in the delivery passage of the finely powdered drug so as to prevent the breathing difficulty when taking air.

At this time, the air 19*c* taken through the air-intake aperture 15*c* with the whistle 16 attached thereto simultaneously flows in the whistle 16. Thereafter, the air flows in the mouthpiece 14a after passing through the whistle 16 and is delivered in the oral cavity of the patient as the air 19.

FIG. 14 is a diagram showing the flow of the air and the drug inside the inhaler when the drug is inhaled by using the asthma drug inhaler with a whistle according to the present invention shown in FIG. 13. The patient inhales the air with holding the mouthpiece 14a in the mouth.

Then, the air 19a flows in through the air hole 15e provided at the lower part of the tube body 15a, and the air 19a passes the inhaled drug tube 15b and flows in the mouthpiece 14a. At this time, the air 19a flown through the air hole 15e into the inhaled drug tube 15b winds up the finely powdered drug 19e in the inhaled drug tube 15b and flows in the mouthpiece 14a together with the drug 19e.

At the same time with the inflow of the air 19a through the air hole 15a, the air 19b is taken in through the four air-intake apertures 15c provided in the upper parts of the outer peripheral surface of the tube body 15a. Simultaneously, the air 19c flows also in the whistle 16 attached to the air-intake aperture 15c. Therefore, when the air 19d flows out from the whistle 16, the sound 19f like "beep" is emitted by the vibration of the protrusion in the whistle 16.

The finely powdered drug 19e in the inhaled drug tube 15b wound up by the air 19a flown in through the air hole 15e flows in the mouthpiece 14a together with the air 19a through the drug inlet 14d provided at the center of the mouthpiece 14a, and the drug 19e is dispersed by generating the spiral flow from the spiral-shaped groove 14c and then is delivered in the oral cavity.

The case where the whistle 16 is attached to one of the air-intake apertures 15c provided in the tube body 15a has been described here. However, it is also possible to provide the whistle 16 to any of the four air-intake apertures 15c and the number of the whistles attached is not limited to one, and it is possible to provide several whistles.

In addition, since the position to which the whistle 16 is attached is not limited if it is located on the air passage below the mouthpiece 14a, the whistle can be attached to the air hole 15e not to the air-intake aperture 15c.

Figure 15:
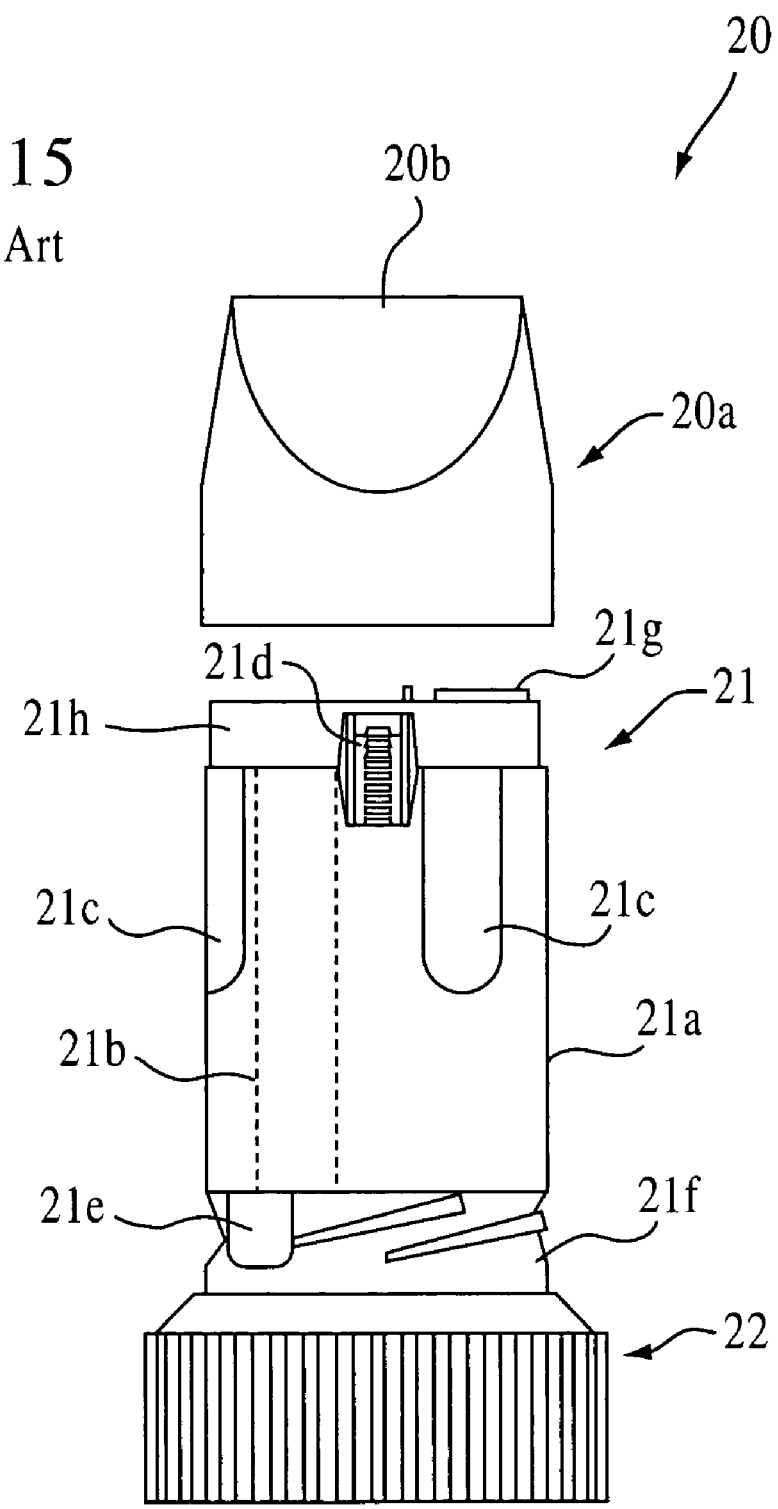
FIG. 15 is an exploded front view of a conventional inhaler.

As described above, the asthma drug inhaler with a whistle 14 shown in FIGS. 10 to 14 according to another embodiment of the present invention is realized by attaching a whistle to the asthma drug inhaler 20 shown in FIGS. 15 and 16. However, not only the asthma drug inhaler 20 but also the other inhalers can be used to provide the asthma drug inhaler with a whistle if the inhalers have a structure in which the air is taken in from the upper part and the lower part of the main body located below the mouthpiece.

More specifically, if the inhaler has a structure in which the air is taken in from the upper stream of the air passage, the inhaler can be used to provide the asthma drug inhaler with a whistle by attaching a whistle to an air-intake part such as the air-intake aperture.

The present invention has the structure as described above. So, the advantages as follows can be accomplished. First, the asthma drug inhaler with a whistle according to the present invention makes it possible to check whether or not the patient him/herself can sufficiently inhale the drug owing to the sound emitted from the whistle.

Second, it is possible to explain how to handle the inhaler in an easily understood manner for such patients as the children and the elderly, who cannot handle the inhaler, by explaining that a sound is emitted when the drug is appropriately inhaled.

Third, since the whistle is designed to be detachable, the patient who gets accustomed to handing the inhaler can use the inhaler without attaching the whistle.

Fourth, in the case of the inhaler having a structure in which openings for air intake are provided in the mouthpiece and the air is taken in from the lower stream of the air passage, the whistle can be attached to the opening, and in the case of the inhaler having a structure in which air holes and air intake apertures for taking air are provided in the parts of the main body below the mouthpiece and the air is taken in from the upper stream of the air passage, the whistle can be attached to the parts of the main body. Therefore, almost all types of the inhalers for inhaling the drug by the patient him/herself can be used to provide the asthma drug inhaler with a whistle.

What is claimed is:

1. An asthma drug inhaler with a whistle, comprising; a mouthpiece with a mouthpiece opening and at least one air intake opening, and a whistle attached to said at least one air intake opening provided at a part of the mouthpiece located on an inhalation passage of a finely powdered drug,
   wherein the whistle comprises a partition wall, an air vent, a hollow resonant chamber, and a protrusion, and
   wherein the whistle makes a sound when the inhalation is properly done.

2. An asthma drug inhaler according to claim 1, wherein said whistle is removable, such that a whistle sound is not made when the whistle is removed.

3. An asthma drug inhaler according to claim 1 further comprising a drag delivery opening for introducing air to take up a finely powdered drug into a delivery passage, wherein said at least one air intake opening provides air to correct the difference between the lung capacity in the inhalation and the air flow rate in the delivery passage of the finely powdered drug as to prevent breathing difficulty.

4. An asthma drag inhaler according to claim 1, wherein said mouthpiece has two air intake openings.

5. An asthma drug inhaler according to claim 4, wherein said whistle may be removed from or placed in either of said two air intake openings in said mouthpiece.

6. An asthma drug inhaler with a whistle, comprising:
   a drug delivery opening for introducing air to take up a finely powdered drug into a delivery passage, a mouthpiece opening, and an air intake opening to provide air to correct the difference between the lung capacity in the inhalation and the air flow rate in the delivery passage of the finely powdered drug as to prevent breathing difficulty,
   wherein the whistle comprises a partition wall, an air vent, a hollow resonant chamber, and a protrusion,
   wherein said whistle is attached to said air intake opening, and
   wherein the whistle makes a sound when the inhalation is properly done.

7. An asthma drug inhaler according to claim 6, wherein said whistle is removable, such that a whistle sound is not made when the whistle is removed.

8. An asthma drug inhaler according to claim 7 having four air intake openings to provide air to correct the difference between the lung capacity in the inhalation and the air flow rate in the delivery passage of the finely powdered drug as to prevent breathing difficulty.

9. An asthma drug inhaler according to claim 8, further comprising a main body and a mouthpiece, wherein said four air intake openings are oblong in shape and are located in a main body of the inhaler, upstream of said mouthpiece.

10. An asthma drug inhaler according to claim 9, wherein said whistle can be inserted into and removed from any of said four air intake openings.

* * * * *